(12) United States Patent
Cuckle

(10) Patent No.: US 8,876,714 B2
(45) Date of Patent: Nov. 4, 2014

(54) SYSTEMS AND METHODS FOR ASSESSING RISK OF CHROMOSOMAL DISORDERS

(75) Inventor: Howard Stephen Cuckle, Harrogate (GB)

(73) Assignee: Wallac Oy, Turku (FI)

(*) Notice: Subject to any disclaimer, the term of this patent is extended or adjusted under 35 U.S.C. 154(b) by 117 days.

(21) Appl. No.: 12/888,481

(22) Filed: Sep. 23, 2010

(65) Prior Publication Data
US 2011/0208053 A1    Aug. 25, 2011

Related U.S. Application Data

(60) Provisional application No. 61/306,747, filed on Feb. 22, 2010.

(51) Int. Cl.
| | |
|---|---|
| *A61B 8/00* | (2006.01) |
| *A61B 8/08* | (2006.01) |
| *A61B 5/107* | (2006.01) |
| *A61B 5/055* | (2006.01) |
| *G06F 19/00* | (2011.01) |

(52) U.S. Cl.
CPC .............. *A61B 5/1075* (2013.01); *A61B 5/055* (2013.01); *A61B 8/0866* (2013.01); *A61B 2503/02* (2013.01); *G06F 19/3431* (2013.01)
USPC ........................................................ 600/437

(58) Field of Classification Search
USPC .......................................... 600/437; 382/128
See application file for complete search history.

(56) References Cited

U.S. PATENT DOCUMENTS

| | | |
|---|---|---|
| 5,506,150 A | 4/1996 | Canick |
| 5,605,843 A | 2/1997 | Canick |
| 5,716,853 A | 2/1998 | Cuckle |
| 6,025,149 A | 2/2000 | Cuckle |
| 2005/0074783 A1 | 4/2005 | Orlandi |
| 2005/0245825 A1* | 11/2005 | Krantz et al. ................. 600/443 |
| 2007/0148631 A1 | 6/2007 | Wright |
| 2009/0036748 A1* | 2/2009 | Pergament et al. ........... 600/300 |
| 2010/0304412 A1 | 12/2010 | Cuckle |

FOREIGN PATENT DOCUMENTS

WO          9412884          6/1984

OTHER PUBLICATIONS

Spencer, "Screening for trisomy 21 in twin pregnancies in the first trimester using free beta-hCG and PAPP-A, combined with fetal nuchal translucency thickness"; Prenat. Diag. 20:91-95, 2000.*
Spencer et al., "Screening for trisomy 21 in twins using first trimester ultrasound and maternal serum biochemistry in a one-stop clinic; a review of three years experience", BJOG, vol. 110, pp. 276-280, Mar. 2003.*
Maymon et al. ("Integrated first- and second-trimester Down syndrome screening test among unaffected IVF pregnancies", Prenatal Diagnosis, vol. 24: p. 125-129, 2004).*
ISR/WO for PCT/IB/2010/002414 dated Feb. 7, 2011.

(Continued)

*Primary Examiner* — Jonathan Cwern
(74) *Attorney, Agent, or Firm* — Rhodes IP PLC; Christopher R Rhodes

(57) ABSTRACT

Certain aspects and examples are directed to systems and methods for assessing risk of chromosomal disorders. Certain embodiments are directed to systems and methods that use nuchal translucency values from both twins to provide a fetus specific risk of a chromosomal disorder in at least one fetus of the twins fetuses.

22 Claims, 9 Drawing Sheets

(56) References Cited

OTHER PUBLICATIONS

Wojdemann et al. Prenatal Diagnosis, vol. 26, Jan. 1, 2006, pp. 218-220.
Larsen et al. Prenatal Diagnosis, vol. 18, Jan. 1, 1998, pp. 706-712.
Cuckle and Maymon. Prenatal Diagnosis, vol. 30, Jan. 1, 2010, pp. 827-833.
Casasbuenas et al. Ultrasound Med. 27(3), 363-369, 2008.
Cheng et al. Prenat. Diagn., 30(3): 247-250, 2010.
Cuckle et al. Br. J. Obstet Gyn., 94, 387-401, 1987.
Dyole et al. J. Epid. Comm. Health, 45, 43-48, 1990.
Elwood, J.M. Obstet. Gynaecol., 85(5), 351-358, 1978.
Garchet-Beaudron et al. Prenat. Diagn., 28(12), 1105-9, 2008.
Gonce et al. Prenat. Diagn., 25, 1156-1161, 2005.
Hey et al. Am. J. Hum. Genet., 22, 662-678, 1970.
Hui et al. Prenat. Diagn. 26(6), 510-513, 2006.
Linskens et al. Prenat. Diagn., 29(1), 74-78, 2009.
Logghe et al. Prenat. Diagn., 23, 389-392, 2003.
Loos et al. Twin Res. 1, 167,175, 1998 (abstract only).
Machin et al. Am. J. Med. Genet, 55(1), 71-76, 1995.
Meyers et al. Obstet. Gynecol., 89, 248-251, 1997 (abstract only).
Monni et al. Croat. Med. J., 41(3), 266-269, 2000.
Mutton et al. J. Med. Genet., 33(5), 387-394, 1996.
National Center for Health Statistics, DHHS Publication 92-1928, 1992.
Orlandi et al. Prenat. Diagn., 22(8), 718-721, 2002.
Pandya et al. J. Ultrasound. Med., 14, 565-568, 1995 (abstract only).
Russell et al. Obstet. Gynecol, 101(1), 129-135 (2003 (abstract only).
Sebire et al. Br. J. Obstet. Gyn., 103, 999-1003, 1996.
Sebire et al. Ultrasound Obstet. Gynecol., 10(2), 86-89, 1997.
Spencer et al. Br. J. Obstet. Gynecol., 110(3), 276-280, 2003.
Spencer et al. Ultrasound Obstet. Gynecol., 22, 142-148, 2003.
Sperling et al. Ultrasound Obstet. Gynecol., 29(5), 517-526, 2007.
Stenhouse et al. Ultrasound Obstet. Gynecol., 19(4), 350-352, 2002.
Sundstrom et al., Acta Obstet. Gynecol. Scand., 88(6), 700-706, 2009.
Vitthala et al. Hu,. Reprod. Update, 15(1), 45-55, 2009.
Windham et al. Genet. Med. Gemellol (Roma), 33(1), 87-95, 1984 (abstract only).
Wojdemann et al. Prenat. Diagn., 26(3), 218-220, 2006.
Wright et al. Ultrasound Obstet Gynecol., 31(4), 376-383, 2008.
Wright et al. Hum. Reprod., 19(8), 1831-1836, 2004.
Wojdemann et al. Prenat. Diagnosis, vol. 26, Jan. 1, 2006, pp. 218-220.
Official Action EP10779808.7.
Spencer, Kevin. Prenat. Diagn 20: 91-95, 2000.
Cuckle et al. Down's Screening News. 13:1:8, 2006.

* cited by examiner

Table 1

| | DZ | MZ |
|---|---|---|
| MC | 0% | 100% |
| DC, different gender | 100% | 0% |
| DC, same gender | | |
| IVF, MET | 99.3% | 0.7% |
| IVF, SET | 0% | 100% |
| Spontaneous, Caucasian | $0.51 \times z / [0.51 \times z + 0.29 \times 0.4]$ | $0.29 \times 0.4 / [0.51 \times z + 0.29 \times 0.4]$ |
| Spontaneous, Afro-Caribbean | $1.54 \times 0.51 \times z / [1.54 \times 0.51 \times z + 0.29 \times 0.4]$ | $0.29 \times 0.4 / [1.54 \times 0.51 \times z + 0.29 \times 0.4]$ |

$y = 3.602 - 0.4236x + 0.01871x^2 - 0.0002344x^3$, $x$ = maternal age.
$z = y - 0.4$

FIG. 7

Table 2

| | Example 1 | | Example 2 | | Example 3 | |
|---|---|---|---|---|---|---|
| | Fetus 1 1.7 MoM | Fetus 2 1.5 MoM | Fetus 1 1.7 MoM | Fetus 2 1.0 MoM | Fetus 1 1.5 MoM | Fetus 2 1.0 MoM |
| MC | 45 | 45 | 55 | 55 | 1000 | 1000 |
| DC, different gender | 310 | 2800 | 6 | 4400 | 110 | 13,000 |
| DC, same gender | 300 | 2000 | 10 | 2800 | 110 | 10,000 |
| IVF, MET | 45 | 45 | 55 | 55 | 1000 | 1000 |
| IVF, SET | 120 | 160 | 8 | 200 | 140 | 3100 |
| Spontaneous | 140 | 220 | 7 | 270 | 130 | 3000 |
| Afro-Caribbean | 20 | 220 | 20 | 13,000 | 220 | 13,000 |
| Independent | | | | | | |

FIG. 9

SYSTEMS AND METHODS FOR ASSESSING RISK OF CHROMOSOMAL DISORDERS

PRIORITY APPLICATION

This application claims priority to U.S. Provisional Application No. 61/306,747 filed on Feb. 22, 2010, the entire disclosure of which is hereby incorporated herein by reference for all purposes.

TECHNOLOGICAL FIELD

Certain features, aspect and embodiments are directed to systems and methods for assessing risk of chromosomal disorders. In particular, certain embodiments are directed to using nuchal translucency measurements from both twins to assess a risk of a disorder in a specific fetus of the twins.

BACKGROUND

Chromosomal disorders can occur where a fetus has fewer than normal chromosomes, additional chromosomes or mutant chromosomes. Where twins are presents, diagnosis of chromosomal disorders remains difficult because the presence of a normal fetus and an abnormal fetus can skew test results for each fetus.

SUMMARY

In one aspect, an ultrasound system comprising an ultrasound transducer, and a processor electrically coupled to the ultrasound transducer and configured to determine nuchal translucency values and provide a risk of a chromosomal abnormality in each of a first fetus and a second fetus of twin fetuses using first, second and third determined likelihood ratios using the nuchal translucency values, in which the processor is configured to determine the first likelihood ratio based on the first fetus including the chromosomal abnormality and a second fetus being normal, is configured to determine the second likelihood ratio based on the first fetus being normal and the second fetus including the chromosomal abnormality and is configured to determine the third likelihood ratio based on the first fetus including the chromosomal abnormality and the second fetus including the chromosomal abnormality is provided. In some embodiments, the chromosomal disorder can be Down's syndrome, Turner syndrome, Edwards Syndrome, Trisomy 13, triploidy, or a sex chromosome abnormality.

In certain embodiments, the system can include a memory unit electrically coupled to the processor, the memory unit comprising a bivariate Gaussian distribution that is used to determine the first, second and third likelihood ratios. In some embodiments, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM−mean)/s], "u" represents unaffected, "a" represents affected, and ½ represents the fetus. In certain examples, the processor can be further configured to determine the nuchal translucency values for each of the first fetus and the second fetus. In other examples, the memory unit further comprises independently selectable weighting factors for use in determining the first, second and third likelihood ratios. In some embodiments, the system comprises a graphical user interface configured to permit selection of the independently selectable weighting factors. In other embodiments, the system comprises a display screen configured to display signals from the ultrasound transducer. In some examples, the signals can be displayed as a two-dimensional image. In certain examples, pixel positions of the display screen are used to determine nuchal translucency values. In other examples, the nuchal translucency values can be determined automatically by marking pixel positions on the two-dimensional image. In certain embodiments, the risk of a chromosomal abnormality in each of a first fetus and a second fetus of twin fetuses can be determined automatically by marking pixel positions on the two-dimensional image.

In another aspect, a method of assessing a risk of a chromosomal abnormality in twin fetuses using nuchal translucency measurements from a first fetus and a second fetus, the method comprising determining a first likelihood ratio based on the first fetus including the chromosomal abnormality and a second fetus being normal, determining a second likelihood ratio based on the first fetus being normal and the second fetus including the chromosomal abnormality, determining a third likelihood ratio based on the first fetus including the chromosomal abnormality and the second fetus including the chromosomal abnormality, and determining a risk of the chromosomal abnormality in each of the first fetus and the second fetus using the first, second and third determined likelihood ratios is described. In some embodiments, the chromosomal abnormality can be Down's syndrome, Turner syndrome, Edwards Syndrome, Trisomy 13, triploidy, or a sex chromosome abnormality.

In certain embodiments, the first, second and third likelihood ratios can be determined from nuchal translucency ultrasound measurements of the first fetus and the second fetus and by using a bivariate log Gaussian distribution. In some embodiments, the first, second and third likelihood ratios can be determined from nuchal translucency magnetic resonance imaging measurements of the first fetus and the second fetus. In other embodiments, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM−mean)/s], "u" represents unaffected, "a" represents affected, and ½ represents the fetus. In certain examples, each of the first, second and third likelihood ratios are individually weighted to determine the risk of the of the chromosomal abnormality. In other examples, weighting factors based on at least one of maternal age, chorionicity, zygocity, the use of assisted reproductive technologies and ethnicity are used to weight the likelihood ratios. In additional examples, the method can include performing at least one blood test to determine the risk of the chromosomal abnormality. In other examples, the method can include performing amniocentesis. In further examples, the method can include performing chorionic villi sampling. In some examples, the method can include determining the risk of the chromosomal abnormality for each of the first fetus and the second fetus independently from the nuchal translucency values. In other examples, the method can include comparing the determined risk with a risk determined using logistic regression.

In an additional aspect, a device comprising a memory unit, and a processor electrically coupled to the memory unit and configured to assess the risk of a chromosomal disorder in twin fetuses by determining a likelihood ratio for a first, second and third condition using nuchal translucency values from a first fetus and a second fetus of the twin fetuses and using a bivariate Gaussian distribution stored in the memory unit, the first condition where the first fetus is affected with the chromosomal disorder and the second fetus is not affected by the chromosomal disorder, the second condition where the second fetus is affected with the chromosomal disorder and the first fetus is not affected with the chromosomal disorder, and the third condition where the first and second fetuses are both affected with the chromosomal disorder is provided. In some embodiments, the chromosomal disorder can be Down's syndrome, Turner syndrome, Edwards Syndrome, Trisomy 13, triploidy, or a sex chromosome abnormality.

In certain examples, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM−mean)/s], "u" represents unaffected, "a" represents affected, and ½ represents the fetus. In certain embodiments, the distribution stored in the memory unit can be a bivariate log Gaussian distribution. In other embodiments, the device can be configured as a cellular phone. In some embodiments, the device can be configured to assess the risk using a two-dimensional picture captured by the device. In other embodiments, the device can be configured to output a log MoM value using the nuchal translucency values and the bivariate Gaussian distribution.

In another aspect, a device configured to provide a risk of a chromosomal disorder in each of a first fetus and a second fetus of twin fetuses from at least three likelihood ratios comprising a first likelihood ratio where both fetuses are considered but only the first fetus is affected with the chromosomal disorder, a second likelihood ratio where both fetuses are considered but only the second fetus is affected with the chromosomal disorder, and a third likelihood ratio where both fetuses are considered and both fetuses are affected with the chromosomal disorder is disclosed. In some embodiments, the chromosomal disorder can be Down's syndrome, Turner syndrome, Edwards Syndrome, Trisomy 13, triploidy, or a sex chromosome abnormality.

In certain examples, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM−mean)/s], "u" represents unaffected, "a" represents affected, and ½ represents the fetus. In certain embodiments, the device can include an ultrasound transducer. In other embodiments, signals from the ultrasound transducer can be provided to a processor and used to determine the likelihood ratios. In some embodiments, the processor can be configured to determine nuchal translucency values from the provided signals and determine the likelihood ratios using the determined nuchal translucency values and a bivariate Gaussian distribution. In some embodiments, the device can be configured as a cellular phone.

In an additional aspect, use of a bivariate Gaussian distribution of nuchal translucency measurements with ultrasound nuchal translucency measurements of twin fetuses to assess a risk of a chromosomal abnormality in each of a first fetus and a second fetus of the twin fetuses by determining a first likelihood ratio based on the first fetus including the chromosomal abnormality and a second fetus being normal, determining a second likelihood ratio based on the first fetus being normal and the second fetus including the chromosomal abnormality, determining a third likelihood ratio based on the first fetus including the chromosomal abnormality and the second fetus including the chromosomal abnormality, and determining a risk of the chromosomal abnormality in each of the first fetus and the second fetus using the first, second and third determined likelihood ratios is described. In some embodiments, the chromosomal disorder can be Down's syndrome, Turner syndrome, Edwards Syndrome, Trisomy 13, triploidy, or a sex chromosome abnormality.

In certain examples, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM−mean)/s], "u" represents unaffected, "a" represents affected, and ½ represents the fetus. In some examples, at least one weighting factor based on maternal age, the use of assisted reproductive technologies, ethnicity, history, chorionicity, and fetus gender can be used. In other examples, each fetuses risk of having Down's syndrome can be determined In additional examples, each fetuses risk of having one or more of Turner syndrome, Edwards Syndrome, Trisomy 13, triploidy, or a sex chromosome abnormality can be determined In additional examples, the determined risk can be compared to the results of one or more fluid tests.

In another aspect, a method of assessing the fetal risk, in each of twin fetuses, of having a chromosomal disorder, the method comprising using nuchal translucency values from both of the twin fetuses with a bivariate log Gaussian distribution to determine the fetal risk of the chromosomal disorder in each of the twin fetuses is provided. In some embodiments, the chromosomal disorder can be Down's syndrome, Turner syndrome, Edwards Syndrome, Trisomy 13, triploidy, or a sex chromosome abnormality.

In certain embodiments, the nuchal translucency values can be used to determine each fetuses risk of having Down's syndrome. In other embodiments, a probability of only the first fetus of the twin fetuses having Down's syndrome, a probability of only a second fetus of the twin fetuses having Down's syndrome, and a probability of both the first fetus and the second fetus having Down's syndrome can be used to determine the risk of Down's syndrome for each fetus. In additional embodiments, a likelihood ratio of only the first fetus of the twin fetuses having Down's syndrome, a likelihood ratio of only a second fetus of the twin fetuses having Down's syndrome, and a likelihood ratio of both the first fetus and the second fetus having Down's syndrome can be used to determine the risk of Down's syndrome for each fetus. In some embodiments, the likelihood ratios can be determined using the following equation:

$$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM–mean)/s], "u" represents unaffected, "a" represents affected, and ½ represents the fetus. In some embodiments, weighting factors can be used to determine the risk of Down's syndrome for each fetus.

Additional features, aspects, examples and embodiments are described in more detail below.

BRIEF DESCRIPTION OF THE FIGURES

Certain illustrative embodiments are described in more detail below with reference to the accompanying figures in which:

FIG. 7 is a table (Table 1) showing the proportions of dizygotic (DZ) and monozygotic (MZ) twins according to chorionicity, fetal gender, assisted reproduction or spontaneous, maternal age and ethnicity, in accordance with certain examples;

FIG. 9 is a table (Table 2) showing examples of fetus-specific Down's syndrome risk at term (1 in n) for a woman aged 25 years scanned at 12 weeks using both NTs and each independently, in accordance with certain examples.

DETAILED DESCRIPTION

Figure 1:
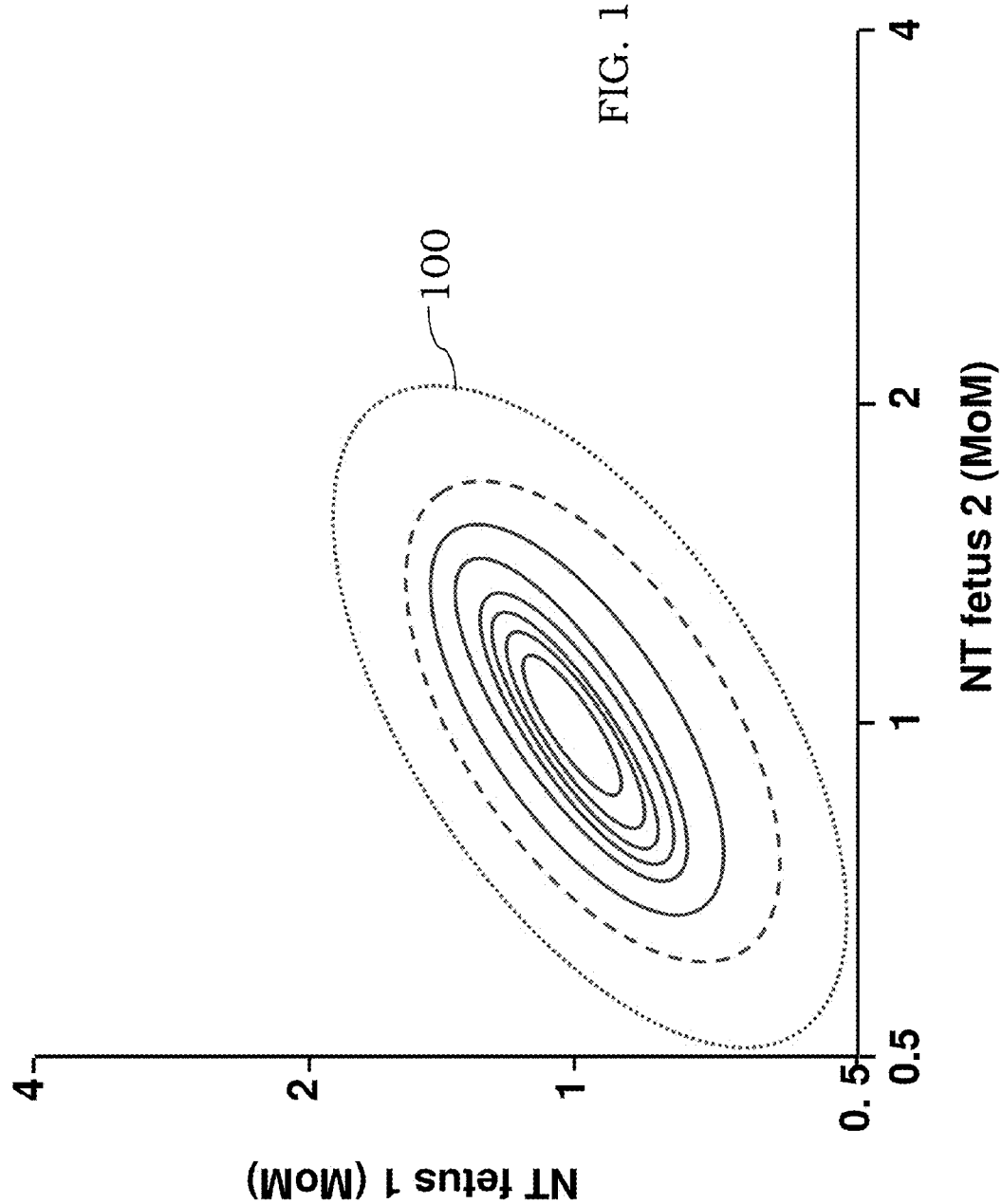
FIG. 1 is graph showing a bivariate distribution where both fetuses are not affected by a chromosomal disorder, in accordance with certain examples.

Certain features and advantages of the methods, devices and systems described herein can permit determination of the risk of a fetus having a particular disorder or disease, e.g., a chromosomal disorder or disease. In some embodiments, the risk can be more accurately determined by using nuchal translucency values of both twins when determining the risk for an individual fetus of the twins.

Maternal serum screening for Down's syndrome has much lower performance characteristics in twin pregnancies compared with singletons. For example, modelling predicts that in 30 year old women second trimester α-fetoprotein (AFP), unconjugated estriol (uE$_3$), free-β human chorionic gonadotrophin (hCG) and inhibin with a 1 in 250 term cut-off risk will detect just one-quarter of affected twin pregnancies compared with two-thirds in singletons, albeit with fewer false-positives. The reason for the poorer results is that in twins that are discordant for Down's syndrome feto-placental products from the unaffected fetus can mask the abnormal levels produced by the affected fetus.

In contrast, first trimester ultrasound nuchal translucency (NT) screening is fetus-specific and is therefore regarded as the method of choice for twins. The NT and crown-rump length (CRL) measurements of each fetus are used to calculate the chance that it is affected by Down's syndrome in exactly the same way as a singleton. Even when maternal serum markers are measured concurrently the performance is comparable with singletons. In the above example, if screening was carried out at 11 weeks with NT, free-β hCG and pregnancy associated plasma protein (PAPP)-A the modelling predicts that 72% of affected twins would be detected compared with 77% in singletons with a virtually identical false-positive rate.

However, the fetus-specific of method of calculating Down's syndrome risk in twins assumes that the NT measurements in the two fetuses are independent. A previous study has shown, in a series of 181 unaffected twins from Denmark, a correlation coefficient of 0.34 between the pairs of NTs, expressed in log multiples of the median (MoM) for CRL (Wøjdemann K R, Larsen S O, Shalmi A C, Sundberg K, Tabor A, Christiansen M. Nuchal translucency measurements are highly correlated in both mono- and dichorionic twin pairs. Prenat Diagn 2006; 26(3):218-20). A similar substantial degree of correlation was found both in the 31 monochorionic (MC), with correlation coefficient 0.40, and the 150 dichorionic (DC) twins, with correlation coefficient 0.32. The study by Wøjdemann et al. does not specify how many sonographers participated or whether there were any systematic differences between them in singleton pregnancies. Some, or potentially all, the correlation could have been accounted for by differences between sonographers, with those tending to over-measure NTs doing so for both fetuses and vice versa.

In certain embodiments described herein, fetus-specific chromosomal abnormality risk in fetal twins can be determined by considering a between-fetus nuchal translucency (NT) correlation. The method can involve use of the NT values of both twins when determining the fetus-specific risk for an individual twin. Although certain examples described herein refer to Down's syndrome, it is recognized that the methods are applicable to other chromosomal abnormalities that correlate with NT values. For example, abnormal nuchal translucency measurements have been associated with the following disorders: Down's syndrome (Trisomy 21), congenital heart defects, Turner syndrome, Edwards Syndrome (Trisomy 18), Trisomy 13, triploidy, and sex chromosome abnormalities. The methods and devices described herein can be used to assess the risk of these and other chromosomal abnormalities in twins or in pregnancies including at least two fetuses. Unless otherwise clear from the context, the terms "disorder" and "abnormality" are interchangeable.

In certain embodiments, a bivariate Gaussian model can be used to calculate probabilities and likelihood ratios using between-fetus nuchal translucency values. The bivariate model permits between-fetus correlation. For example, using bivariate models allows the estimation of parameters relating to each trait alone (i.e. VA, h2 etc), but also yields estimates of covariance components between traits. These include the (additive) genetic covariance COVA, which is often rescaled to give the genetic correlation rG. However, correlations among traits can also arise through other random effects (e.g. maternal effects) and these sources can be explicitly modeled in a bivariate analysis as well. In some examples, the bivariate model assumes discordant Down's syndrome (only one fetus has Down's syndrome), whereas in other examples, the bivariate model assumes concordant Down's syndrome (both fetuses have Down's syndrome). Without wishing to be bound by any particular mathematical theory, a bivariate or multivariate Gaussian distribution model permits fit of vector observations. For example, if x and y are random variables, then a bivariate normal probability density function p(x,y) can be represented as $$p(x, y) = \frac{1}{2\pi\sigma_x\sigma_y\sqrt{1-\rho^2}} \exp\left[-\frac{1}{2(1-\rho^2)}Q(x, y)\right]$$

where $\sigma_x$ and $\sigma_y$ represent the standard deviation of x and y, respectively, $\rho$ represents the correlation coefficient and Q(x, y) is a quadratic equation that can be represented as $$Q(x, y) = \left(\frac{x-\mu_x}{\sigma_x}\right)^2 - 2\rho\left(\frac{x-\mu_x}{\sigma_x}\right)\left(\frac{y-\mu_y}{\sigma_y}\right) + \left(\frac{y-\mu_y}{\sigma_y}\right)^2$$

where $\mu_x$ and $\mu_y$ are the mean x and y values, respectively, of the probability distribution. In some examples, a bivariate log distribution may be used based on log MoM NT values.

Using the bivariate normal distribution, a likelihood ratio (LR) can be determined for each fetus having the disorder individually (with the other fetus assumed to not have the disorder) and for both fetuses having the disorder. There are many ways to determine LRs, and LRs may generally be determined by dividing the sensitivity of the test by (1-specificity) or in mathematical form $$LR = \frac{\text{Probability(Test\_Positive, Disorder\_Positive)}}{\text{Probablity(Test\_Positive, Disorder\_Negative)}}$$

A general formula for calculating a likelihood ratio using a bivariate log model can be represented as:

$$LR = \left|\frac{s_{u1}s_{u2}\sqrt{(1-r_u^2)}}{s_{a1}s_{a2}\sqrt{(1-r_a^2)}}\right| \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MOM-mean)/s], "u" represents unaffected, "a" represents affected, and ½ represents the fetus. To determine an overall risk, the pretest odds of a particular diagnosis can be multiplied by the likelihood ratio to determine the risk of having the disorder.

In certain embodiments, a probability for each fetus having a disorder (where the other fetus is assumed to not have the disorder) can be determined from nuchal translucency measurements. These probabilities can be represented by $P_{fetus1only}$ and $P_{fetus2only}$. A probability of both fetuses having the disorder ($P_{both}$) can also be determined using a bivariate log model as described herein. Likelihood ratios for each of the three conditions can also be determined, e.g., $LR_{fetus1only}$ where only fetus 1 is presumed to have the disorder and normal fetus 2 is taken into account, $LR_{fetus2only}$ where only fetus 2 is presumed to have the disorder and normal fetus 1 is taken into account and $LR_{both}$, where both fetus 1 and fetus 2 are presumed to have the disorder and taken into account. The risk for each fetus can then be determined Expressed mathematically, fetus 1's risk can be expressed as $P_{fetus1only}LR_{fetus1only}+P_{both}LR_{both}$ and fetus 2's risk can be expressed as $P_{fetus2only}LR_{fetus2only}+P_{both}LR_{both}$.

By using the likelihood ratios of both fetuses having the disorder in the risk calculations for each fetus having the disorder, the risk of each fetus having the disorder can be more accurately determined where two or more fetuses are present. In certain embodiments, to determine a fetus-specific risk, maternal age-specific probabilities can be expressed as odds, e.g., in the form of probability: (1-probability), and then multiplied by the appropriate likelihood ratios, e.g., $LR_{fetus1only}$, $LR_{fetus2only}$, and $LR_{both}$ to determine a fetus-specific risk.

In certain embodiments, one or more weighting factors can be used in the risk assessment methods. For example, the mother's age, proportion of fraternal or dizygotic (DZ) twins and identical or monozygotic (MZ) twins given chorionicity, gender, ethnicity, whether assisted reproduction or spontaneous pregnancy resulted, etc, can be used in a weighting factor to increase the overall accuracy of the risk assessment. These weighting factors can be used to create a distribution, e.g., zygocity distribution, that is then multiplied by the risk noted above. For example, the risk determined above for fetus 1 ($P_{fetus1only}LR_{fetus1only}+P_{both}LR_{both}$) can be multiplied by the zygocity distribution to obtain a weighted risk that considers other factors. Or expressed mathematically, for fetus 1, the probability that fetus 1 is affected by the disorder can be determined by multiplying the appropriate variables as follows:

$W_{DZ}(P_{x,DZ,fetus1only}LR_{fetus1only}+P_{x,DZ,both}LR_{both})+$
$W_{MZ}P_{x,MZ}LR_{both}$ where $W_{DZ}$ and $W_{MZ}$ are the weighting factors for dizygotic and monozygotic, respectively, $P_{x,DZ,fetus1only}$ is the probability of only fetus 1 having the disorder (assuming dizygotic), $P_x$ is the maternal age-specific probability of Down's syndrome in singletons, $P_{x,DZboth}$ is the probability of both fetuses having the disorder (assuming dizygotic) $P_{x,MZ}$ is the probability assuming monozygotic and both fetuses having the disorder—in MZ twins, both fetuses are assumed to be affected. For fetus 2, the probability that fetus 2 is affected by the disorder can be determined in a similar manner as follows:

$$W_{DZ}(P_{x,DZ,fetus2only}LR_{fetus2only}+P_{x,DZ,both}LR_{both})+W_{MZ}P_{x,MZ}LR_{both}$$

where $P_{x,DZ,fetus2only}$ is the probability of only fetus 2 having the disorder (assuming dizygotic).

In certain embodiments, a user, e.g., a sonographer, would enter characteristic features into the imaging system during nuchal translucency measurements. For example, the sonographer would enter maternal age, chorionicity, and other desired factors into the system. The system would then use the factors in the likelihood risk calculations to determine an overall risk for at least one of the fetuses or for both fetuses.

Certain embodiments herein advantageously use nuchal translucency (NT) measurements along with the models and ratios described herein to assess the risk of chromosomal abnormalities. NT measurements use ultrasound to measure the translucent space in the tissue at the back of a developing fetus around or near the nape of the neck. Fetuses with abnormalities tend to accumulate more fluid at the back of their neck during the first trimester, causing this translucent space to be larger than average. NT scans are typically performed between 11 weeks and 13 weeks and 6 days during the pregnancy.

In a typical NT scan, a sonographer will measure the length of the fetus, e.g., from crown to rump, to determine the fetus's gestational age. A fetus's nuchal fold thickness will increase with fetus age. The ultrasound transducer will be positioned on the mother's abdomen such that the nuchal fold appears on the ultrasound screen, and the thickness of the nuchal fold is then determined A distribution that correlates nuchal translucency thickness with fetal age is typically used to ascertain whether or not the nuchal translucency measurements for a particular fetus are high or within an acceptable window.

In some examples, the nuchal translucency values can be expressed as multiples of the median (MoM). An average value would be expressed as 1 MoM. Thus, nuchal translucency measurements that provide greater than 1 MoM typically indicate a higher risk of the fetus having a chromosomal disorder.

Figure 2:
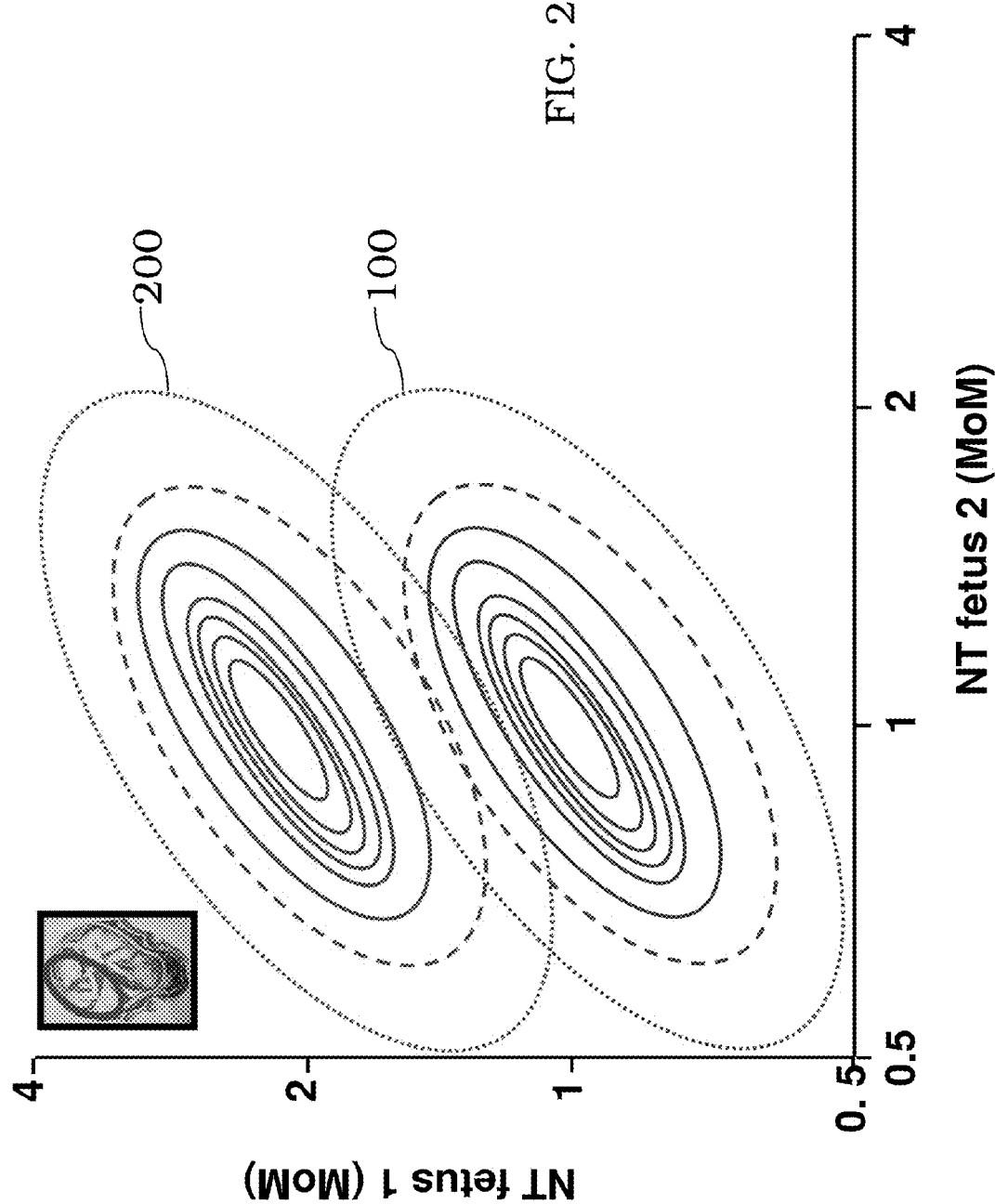
FIG. 2 is graph showing a bivariate distribution where both fetuses are not affected by a chromosomal disorder and a bivariate distribution where fetus 1 is affected by a chromosomal disorder and fetus 2 is unaffected, in accordance with certain examples.
Figure 3:
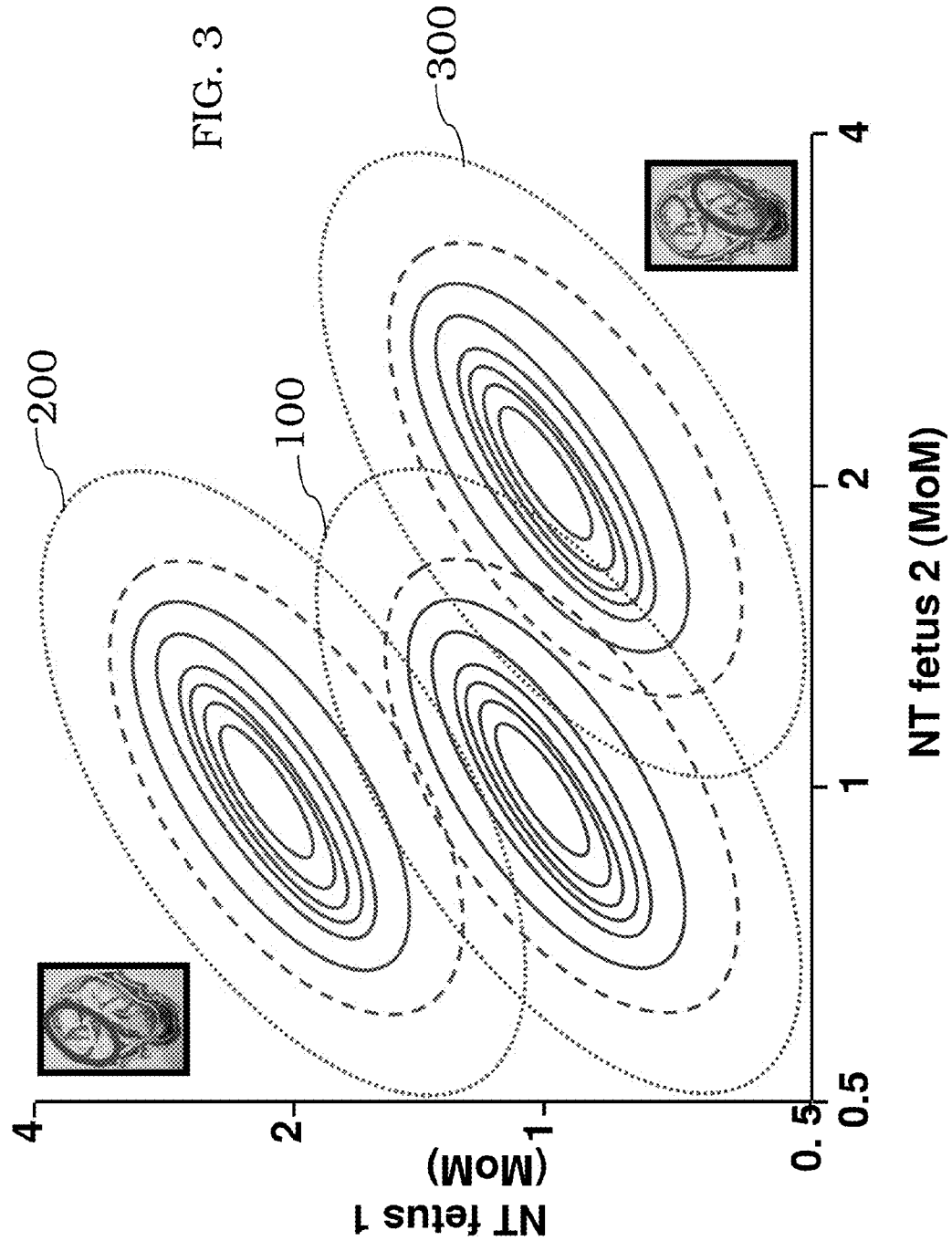
FIG. 3 is graph showing a bivariate distribution where both fetuses are not affected by a chromosomal disorder, a bivariate distribution where fetus 1 is affected by a chromosomal disorder and fetus 2 is unaffected, and a bivariate distribution where fetus 1 is unaffected by a chromosomal disorder and fetus 2 is affected by the chromosomal disorder, in accordance with certain examples.
Figure 4:
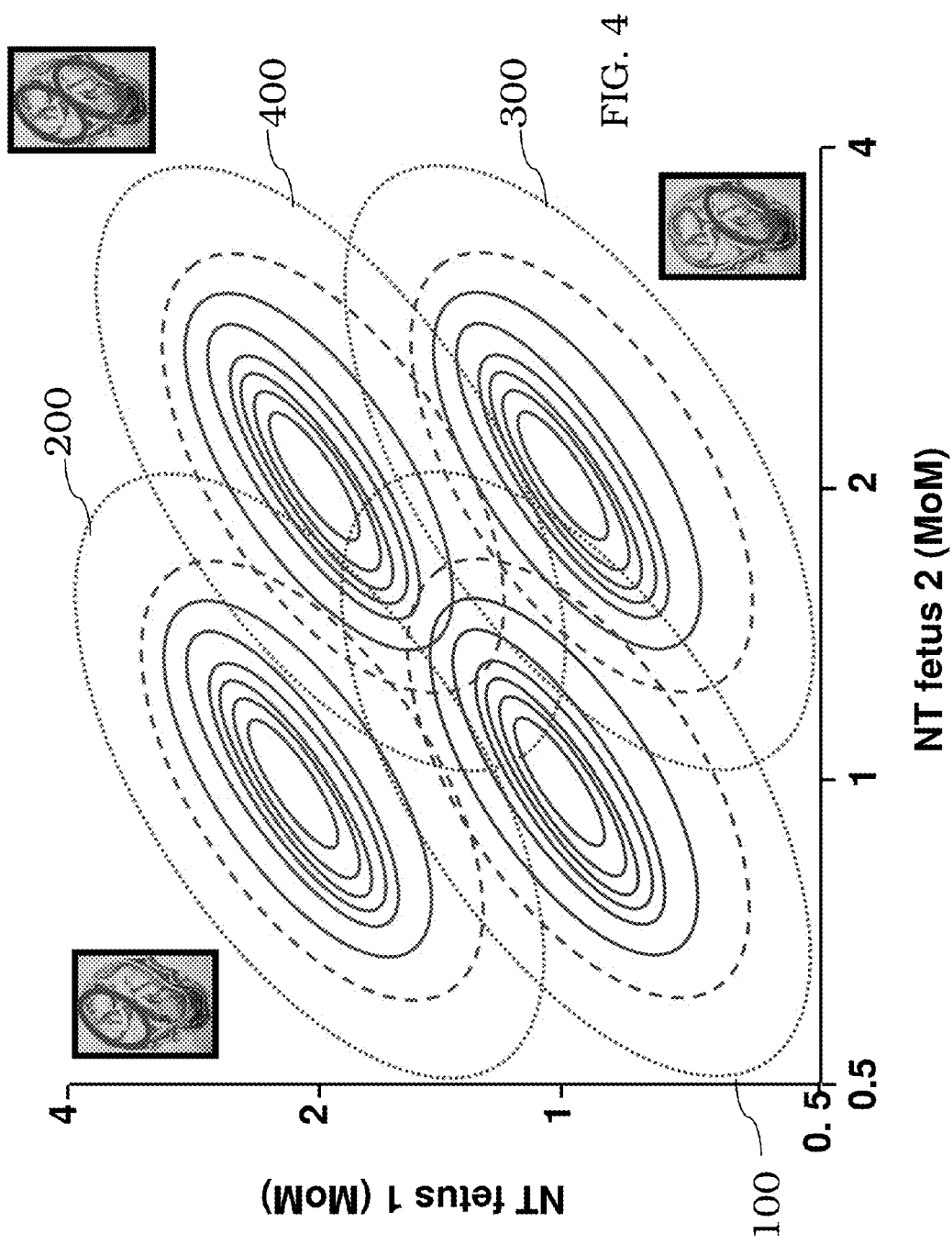
FIG. 4 is graph showing a bivariate distribution where both fetuses are not affected by a chromosomal disorder, a bivariate distribution where fetus 1 is affected by a chromosomal disorder and fetus 2 is unaffected, a bivariate distribution where fetus 1 is unaffected by a chromosomal disorder and fetus 2 is affected by the chromosomal disorder, and a bivariate distribution where fetus 1 and fetus 2 are affected by the chromosomal disorder, in accordance with certain examples.
Figure 5:
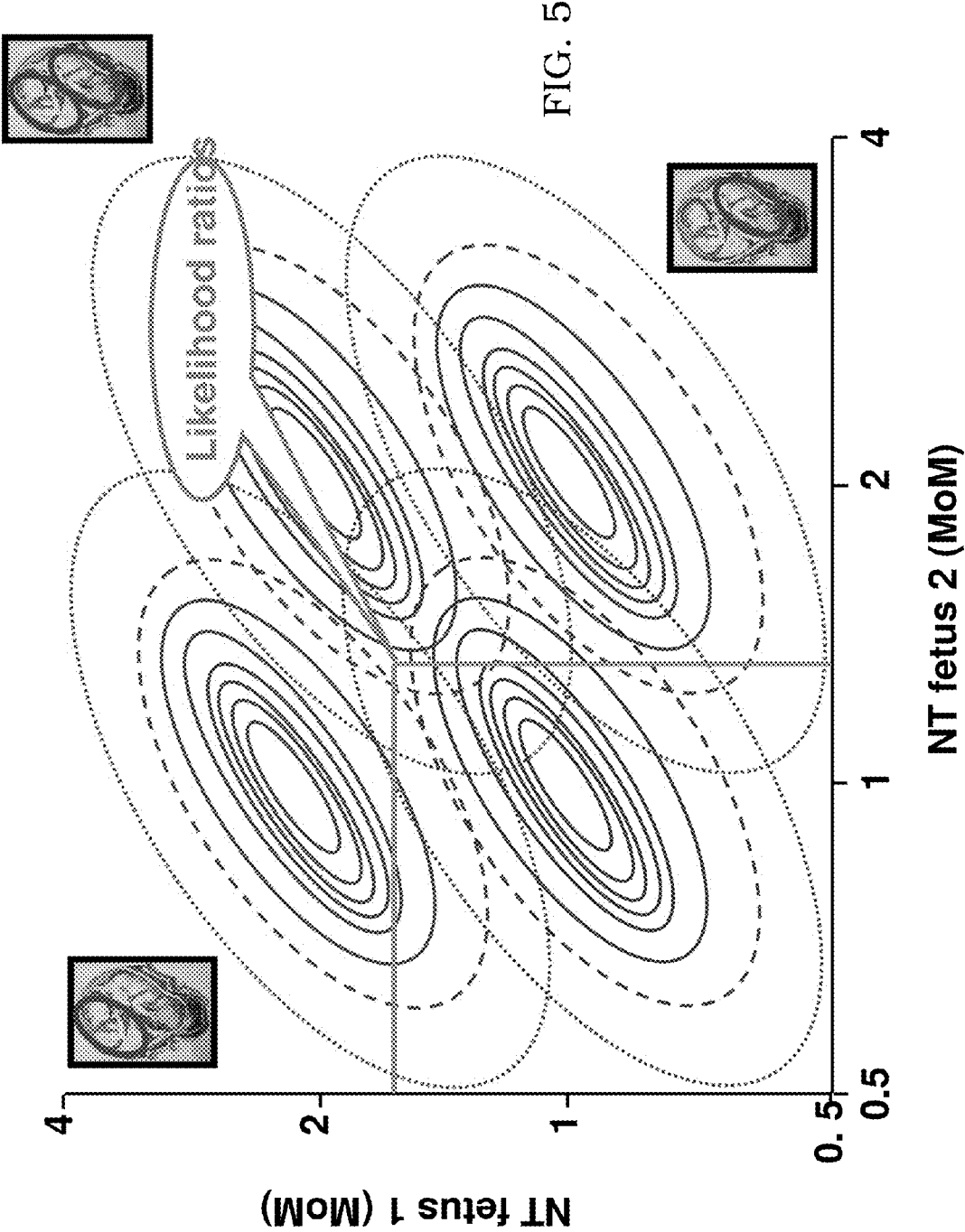
FIG. 5 is a graph pictorially showing a likelihood ratio using the bivariate distributions of FIG. 4, in accordance with certain examples.

In certain examples, a graphical representation of the methodology described herein is shown in FIGS. 1-5. Referring to FIG. 1, a two-dimensional representation 100 is shown where both fetuses are considered unaffected. The mean of this distribution would be centered at 1 MoM. Referring to FIG. 2, a second distribution 200 can be generated where the first fetus (fetus 1) is affected by a chromosomal disorder and the second fetus (fetus 2) is not affected by the chromosomal disorder. Fetus 1 being affected results in shifting of the distribution upward to higher NT fetus 1 values. Referring to FIG. 3, a third distribution 300 can be generated where the first fetus (fetus 1) is unaffected by a chromosomal disorder and the second fetus (fetus 2) is affected by the chromosomal disorder. Fetus 2 being affected results in shifting of the distribution to the right to higher NT fetus 2 values. Referring to FIG. 4, a fourth distribution 400 can be generated where both fetus 1 and fetus 2 are affected by the chromosomal disorder. When both fetuses are affected, the distribution shifts up and to the right. The distributions shown in FIG. 4 can be used to determine likelihood ratios for each of three conditions: (i) where fetus 1 is affected and fetus 2 is unaffected; (2) where fetus 1 is unaffected and fetus 2 is affected; and (3) where both fetuses are affected. FIG. 5 graphically shows the point corresponding to a given pair of nuchal translucency MoM values from fetus 1 and fetus 2. At that point there are three LRs, computed from the ratio of the heights of each of the three affected bivariate distributions (only fetus 1 affected, only fetus 2 affected and both fetuses affected) divided by the height of the unaffected bivariate distribution.

Figure 6:
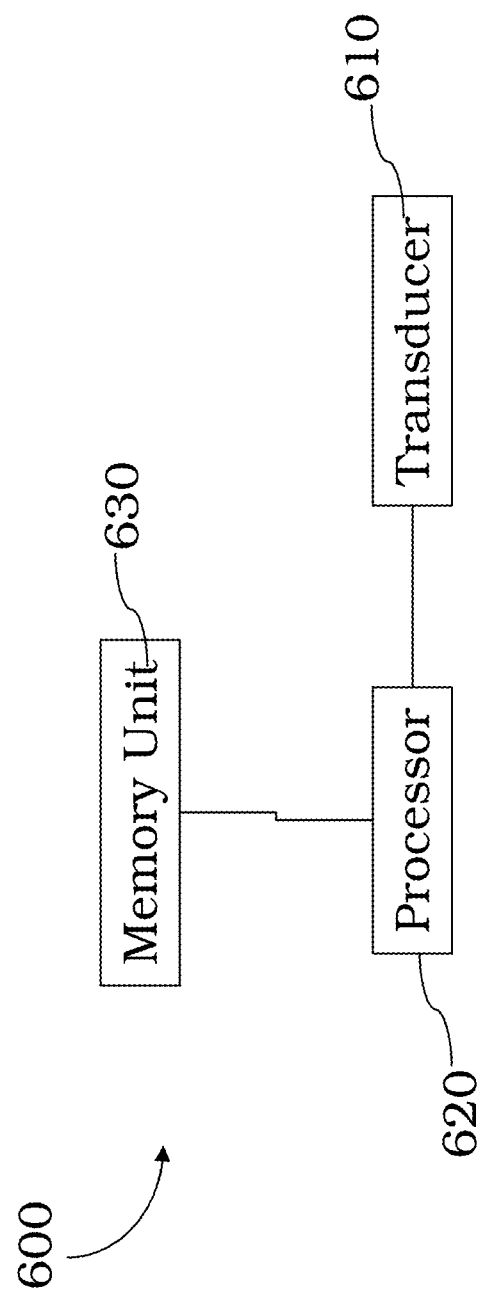
FIG. 6 is a diagram of an ultrasound system, in accordance with certain examples.

In certain embodiments, the fetus-specific risk of a chromosomal disorder can be assessed using an ultrasound system. Referring to FIG. 6, an ultrasound system 600 comprises an ultrasound transducer 610 electrically coupled to a processor 620. The processor 620 is electrically coupled to a memory unit 630, which can include a probability density function generated using the bivariate log Gaussian distribution described herein. In operation, the ultrasound system 600 would be used by a sonographer to perform the nuchal translucency measurements on each fetus. The NT values can be stored, at least for some period, in the memory unit 630 and used to provide a fetus-specific risk for one or both of the fetuses using the bivariate model described herein. If desired, the risk based on independent measurements can also be provided and compared to the risk provided using the nuchal translucency values of both twins when determining the risk for an individual fetus of the twins. Further, in some examples, the sonographer, radiologist or physician may select desired weighting factors to be used in assessing the risk, whereas in other examples, the weighting factors may automatically be used in the risk assessment based on the subject's age, ethnicity, chorionicity, etc. as entered into the system.

While the nuchal translucency measurements are described as being performed using ultrasound, other imaging methods such as three-dimensional ultrasound, four-dimensional ultrasound, magnetic resonance imaging or the like can be used to provide the nuchal translucency measurements. In certain embodiments, the assessed risk can be used, or provided with, other risk assessment methods including imaging methods, blood testing and the like. For example, in Down's syndrome affected fetuses, the femur and humerus may be shortened as compared to non-affected fetuses. Fetus and humerus measurements may be taken using ultrasound at the same time as the nuchal translucency measurements are taken. Similarly, many fetuses having Down's syndrome may not have a fetal nasal bone at 11-13 weeks. Ultrasound measurements can be performed to verify the presence of absence of a fetal nasal bone.

In some examples, fluid testing, e.g., blood testing or amniotic fluid testing, can be performed in addition to the nuchal translucency measurements. The fluid taken from the pregnant woman can be tested for levels of human chorionic gonadotropin, alpha-fetoprotein, estriol, inhibin A, PAPP-A, or the like. Alpha-fetoprotein is produced in the yolk sac and in the fetal liver, and some amount of AFP gets into the mother's blood. In neural tube defects, the skin of the fetus is not intact and so larger amounts of AFP are measured in the mother's blood. In Down syndrome, the AFP is decreased in the mother's blood, presumably because the yolk sac and fetus are smaller than usual. Estriol is a hormone produced by the placenta and is decreased in the Down syndrome pregnancy. Human chorionic gonadotropin hormone is produced by the placenta, and a specific smaller part of the hormone, called the beta subunit, is increased in Down syndrome pregnancies Inhibin A is a protein secreted by the ovary, and the level of inhibin A is increased in the blood of mothers of fetuses with Down syndrome. PAPP-A, which stands for pregnancy-associated plasma protein A, is produced by the covering of a newly fertilized egg, and, in the first trimester, low levels of this protein are present in Down syndrome pregnancies.

In certain examples, amniotic fluid may be withdrawn from the pregnant woman to karyotype the DNA in the fetal cells or otherwise determine if a chromosomal disorder is present in the fetus. Amniocentesis is typically performed between the $14^{th}$ to the $18^{th}$ weeks of pregnancy but may be done sooner or later by some physicians. In other examples, chorionic villus sampling (CVS) can be performed to sample a small amount of the fetal tissue and use the sampled tissue to determine if a chromosomal disorder is present. CVS is typically performed between the $10^{th}$ and $12^{th}$ weeks of pregnancy and may be used in conjunction with the NT measurements to confirm the presence of a chromosomal disorder.

In certain embodiments, the devices, systems and methods described herein may include, or be used with, at least one processor optionally electrically coupled to one or more memory units. In certain examples, the system may be a larger part of a computer system, e.g., part of an ultrasound imaging system or electrically coupled to a network in a hospital or outpatient setting, whereas in other examples, the system may be a stand alone system that includes its own dedicated processor. The computer system may be, for example, a general-purpose computer such as those based on Unix, Intel PENTIUM-type processor, Motorola PowerPC, Sun UltraSPARC, Hewlett-Packard PA-RISC processors, or any other type of processor. In some examples, the processor may be an inexpensive processor that may be programmable to receive inputs from an administrator to configure the system as desired. It should be appreciated that one or more of any type computer system may be used according to various embodiments of the technology. Further, the system may be located on a single computer or may be distributed among a plurality of computers attached by a communications network. A general-purpose computer system may be configured, for example, to perform any of the described functions including but not limited to: nuchal translucency measurements, generation of the bivariate distributions, determination of the likelihood ratios, and the like. It should be appreciated that the system may perform other functions, including network communication, and the technology is not limited to having any particular function or set of functions. In certain embodiments, it may be desirable that the system permit remote access to allow many different users to access the nuchal translucency measurements and/or patient data.

For example, various aspects may be implemented as specialized software executing in a general-purpose computer system. The computer system may include a processor connected to one or more memory units, such as a disk drive, memory, or other device for storing data. The memory unit is typically used for storing programs and data during operation of the device. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between system components of the system. The interconnection device typically is electrically coupled to the processor such that electrical signals may be provided to control operation of the system.

The computer system may also include one or more input devices, for example, a keyboard, mouse, trackball, microphone, touch screen, touch pad, manual switch (e.g., override switch) and one or more output devices, for example, a printing device, display screen, speaker, etc. In addition, the computer system may contain one or more interfaces (not shown) that connect computer system to a communication network in addition or as an alternative to the interconnection device.

The storage system typically includes a computer readable and writeable nonvolatile recording medium in which signals are stored that define a program to be executed by the processor or information stored on or in the medium to be processed by the program. For example, the nuchal translucency measurements, bivariate log distributions, likelihood ratios, weighting factors and the like used in certain embodiments disclosed herein may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in memory system, for example. The processor generally manipulates the data within the integrated circuit memory and then copies the data to the medium after processing is completed. A variety of mechanisms are known for managing data movement between the medium and the integrated circuit memory element, and the technology is not limited thereto. The technology is also not limited to a particular memory system or storage system.

In certain examples, the computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component that can be added to an existing system, e.g., either through software upload or by using a separate module that is added to an existing system such as, for example, an ultrasound imaging system.

Although a computer system is described by way of example as one type of computer system upon which various aspects of the technology may be practiced, it should be appreciated that aspects are not limited to being implemented on any particular type of computer system. Various aspects may be practiced on one or more computers having a different architecture or components than that described herein. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a computer platform for which application programs in high-level programming languages may be written. For example, the technology described herein may be alterable or controllable by a user where the user can select desired weighting factors depending on the particular circumstances. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used.

In certain examples, the hardware or software can be configured to implement cognitive architecture, neural networks or other suitable implementations. One or more portions of the computer system may be distributed across one or more computer systems coupled to a communications network. For example, a remote database may be linked to the system to permit determination of likelihood ratios using data or distributions not stored on-site. These computer systems also may be general-purpose computer systems. For example, various aspects may be distributed among one or more computer systems configured to provide a service (e.g., servers) to one or more client computers, or to perform an overall task as part of a distributed system. In some examples, the ultrasound system may function as a client computer and a remote server may be present at an administrator site to include desired distributions for determining likelihood ratios or other results. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP), Bluetooth, etc. It should also be appreciated that the technology is not limited to executing on any particular system or group of systems. Also, it should be appreciated that the technology is not limited to any particular distributed architecture, network, or communication protocol.

In some examples, various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain embodiments, the methodology described herein can be implemented in a standalone device or in a device that is part of a larger system. For example, a device that includes a memory unit electrically coupled to a processor that is configured to assess the risk of a chromosomal disorder in twin fetuses by determining a likelihood ratio for a first, second and third condition using nuchal translucency values from a first fetus and a second fetus of the twin fetuses and using a bivariate Gaussian distribution can be used. In some examples, the first condition is where the first fetus is affected with the chromosomal disorder and the second fetus is not affected by the chromosomal disorder. In other examples, the second condition is where the second fetus is affected with the chromosomal disorder and the first fetus is not affected with the chromosomal disorder. In further examples, the third condition is where the first and second fetuses are both affected with the chromosomal disorder. In certain embodiments, the distribution can be stored in the memory unit and can be a bivariate log Gaussian distribution as described herein.

In some embodiments, the device can be configured as a cellular phone. For example, a pregnant woman can use a cellular phone to determine the risk of the chromosomal disorder from a two-dimensional picture captured by the device or from a picture uploaded or transferred to the device. In some examples, the device may output a log MoM value using the nuchal translucency values and the bivariate Gaussian distribution, whereas in other examples, the device can be configured to provide various risk levels, e.g., low, average, moderate, or high.

In other embodiments, the device can be configured to provide at least three likelihood ratios comprising a first likelihood ratio where both fetuses are considered but only the first fetus is affected with the chromosomal disorder, a second likelihood ratio where both fetuses are considered but only the second fetus is affected with the chromosomal disorder, and a third likelihood ratio where both fetuses are considered and both fetuses are affected with the chromosomal disorder. As described herein, the device can include an ultrasound transducer or may include other imaging devices. Where an ultrasound transducer is present, signal from the ultrasound transducer can be provided to a processor and used to determine the likelihood ratios. For example, the processor can be configured to determine nuchal translucency values from the provided signals and determine the likelihood ratios using the determined nuchal translucency values and a bivariate log Gaussian distribution.

In some embodiments, the methodology can be implemented in one or more methods or applications that can be downloaded to a mobile device, e.g., an Iphone™ application. Nuchal translucency measurements can be entered into the mobile device by an end user, which may be a patient or a technician for example. Desired weighting factors can be selected from a menu and likelihood ratios can be displayed based on the entered nuchal translucency measurements and the selected weighting factors. In this manner, risk assessment can be performed almost instantly by a user.

The example described below is provide for illustrative purposes only and is not intended to limit the scope of the technology or the claims appended hereto.

EXAMPLE 1

Nuchal translucency values were used to estimate between-fetus correlation coefficient of log NT, in multiples of the median (MoM), from a series of 325 unaffected twins after adjustment for sonographer bias. Between February 2003 and October 2009, a total of 325 women with unaffected twin pregnancies had NT measurements at Leeds Screening Centre, UK. The scans were carried out by four sonographers, two of whom were medically qualified; all were certified by the Fetal Medicine Foundation. NT was expressed in MoMs using a previously published formula (Logghe et al., 2003). Correlation coefficients between the log MoMs were calculated after excluding outliers exceeding the median by at least 3 standard deviations, based on the 90th and 10th centile difference divided by 2.563. A correlation coefficient allowing for sonographer differences was derived by analysis of variance.

In performing the risk calculations, four steps were used: (1) prior probability of Down syndrome in fetus 1 only, fetus 2 only or both fetuses according to maternal age and zygocity; (2) likelihood ratios of Down syndrome in fetus 1 only, fetus 2 only or both, from the two NT MoMs; (3) proportion of dizygotic (DZ) and monozygotic (MZ) twins given chorionicity, gender, whether assisted reproduction or spontaneous, maternal age and ethnicity and (4) multiply the prior probabilities by likelihood ratios and take the weighted average using the zygocity distribution.

For a woman aged x, the maternal age-specific probability of Down syndrome in singletons ($P_x$) is obtained from the birth prevalence curve derived by meta-analysis (Cuckle et al., 1987). In DZ twins, the prior probability of an individual fetus being affected is assumed to be the same as for a singleton, $P_x$, while the probability that the other fetus is affected is assumed to be the probability of Down syndrome recurrence in singletons, $P_x$+0.42% at term (Cuckle and Benn, 2010). It follows that in DZ twins, the probability of both fetuses being affected ($P_{x,DZ,both}$) is $P_x$($P_x$+0.42%), whereas the probability of fetus 1 being affected and fetus 2 unaffected ($P_{x,DZ,1only}$) is $P_x$-$P_{x,DZ,both}$ and is the same for fetus 1 unaffected and fetus 2 affected ($P_{x,DZ,2only}$). At mid-trimester, the recurrence factor is 0.54% instead of 0.42% (Cuckle and Benn, 2010). In MZ twins, both fetuses are assumed to be affected and the probability ($P_{x,MZ}$) is $P_x$.

Likelihood ratios were calculated using the LR formula listed above for scenarios where fetus 1 affected and fetus 2 unaffected ($LR_{1only}$), fetus 1 unaffected and fetus 2 affected ($LR_{2only}$) and both fetuses affected ($LR_{both}$). The LRs were calculated from bivariate log Gaussian distributions of the NT MoMs in fetus 1 and fetus 2 with means and standard deviations used for singleton pregnancies. The Down syndrome means at 11, 12 and 13 weeks of gestation were those derived by meta-analysis, 2.30, 2.10 and 1.92 MoM or 0.362, 0.322 and 0.283 log 10 MoM, respectively (Cuckle and Benn, 2010). The standard deviation of log 10 MoM in unaffected fetuses was 0.070, the value found at Leeds Screening Centre among unaffected singleton pregnancies, and in Down syndrome it was 0.21, derived by adding 0.04 to the unaffected variance (Spencer et al., 2003). For example, at 12 weeks of gestation, the affected pregnancy parameters when calculating $LR_{1only}$ are 0.322 and 0.21 for fetus 1, and 0 and 0.070 for fetus 2; the corresponding unaffected parameters are 0, 0.070, 0 and 0.070.f The correlation coefficient between the log 10 MoMs in unaffected pregnancies was that derived from Leeds Screening Centre data allowing for sonographer differences. In affected twins, it is assumed that the covariance is the same as for unaffected pregnancies.

The proportions of twins which are DZ and MZ were used as weights ($W_{DZ}$ and $W_{MZ}$) in the final step of risk calculation. This is dependent on ultrasound-determined chorionicity, fetal gender differences, whether assisted reproduction or spontaneous pregnancies, maternal age and ethnicity. The proportions are summarized in Table 1 shown in FIG. 7. Chorionicity can be determined by ultrasound examination of the fetal membranes (Stenhouse et al., 2002). The so-called λ sign, caused by invasion of the inter-twin membrane by chorionic villus, is evidence of dichorionicity and either the presence of one amniotic sac or diamniotic sacs with a 'T' sign is evidence of monochorionicity. All MC twin pregnancies can be taken to be MZ: $W_{DZ}$ 0% and $W_{MZ}$ 100%. All DC pregnancies where the fetuses have different genders can be taken to be DZ: $W_{DZ}$ 100% and $W_{MZ}$ 0%. In DC pregnancies with the same gender which are the result of IVF and embryo transfer, the proportions will depend on the number of embryos being transferred.

A study from the Society for Assisted Reproductive Technology (SART) in the United States analyzed data on 39 198 pregnancies resulting from IVF in which information was available on the number of fetal hearts seen on ultrasound (Wright et al., 2004). More than 98% resulted from multiple embryo transfer (MET). There were 15 307 multiple pregnancies, 226 (1.5%) with more fetal hearts than the number of embryos transferred, classified by the authors as MZ, and the remainder with the same number or fewer fetal hearts than embryos transferred were DZ. MET was used in 185 of the presumptively MZ pregnancies and, although not stated in the report, virtually all other multiple pregnancies. In a study of zygocity and chorionicity in 300 twins, 28% (42/152) MZ twins were DC and 58% (86/148) DZ twins had the same gender (Machin et al., 1995). In the much larger East Flanders Prospective Twin Survey, the proportions were 29% (494/1720) and 49% (1487/3047), although assigning the 277 same gender twins of unknown zygocity proportionally as MZ and DZ, the latter is 51% (1615/3175) (Loos et al., 1998). Applying the East Flanders proportions to the SART results, in DC twins of the same gender following IVF with MET, the proportions of DZ and MZ can be taken to be WDZ 99.3% and WMZ 0.7%.

The SART study does not include sufficient information on zygocity following single-embryo transfer (SET). However, the expectation is that all would be MZ with WDZ 0% and WMZ 100%. In spontaneous DC twins with the same gender, the proportions which are DZ and MZ will depend on maternal age and ethnicity. The incidence of MZ twinning in spontaneous pregnancies has been estimated to be 0.4% (Vitthala et al., 2009) and this is unrelated to maternal age (Bortolus et al., 1999) or ethnicity (National Center for Health Statistics, 1992). In contrast, DZ twinning increases with age (Meyers et al., 1997) and varies according to ethnicity. Using national data on twin live births in the United States in 1980 (Russell et al., 2003), we calculated the age-specific DZ twinning incidence by subtracting 0.4%. Standardizing for the maternal age distribution in the Caucasian women, the DZ twinning incidence was 54% higher in the Afro-Americans. The DZ twinning is approximately half as common in women of Oriental origin than in Caucasians (Bulmer, 1970; Elwood, 1978).

The number of maternities and births at each single year of age in England and Wales during 1960 (General Register Office, 1962), before the era of assisted reproduction, was used to calculate the incidence of twinning in Caucasians, expressed in percentage. A cubic regression of incidence on age weighted for the number of maternities yielded: $3.602-0.4236x+0.01871x^2-0.0002344x^3$, where x is the maternal age. The incidence of DZ with the same gender twinning is then estimated by subtracting 0.4% from the regressed incidence and multiplying by 51%, the proportion of DZ with the same gender (Loos et al., 1998), and the incidence of MZ twins that are DC is 0.4% multiplied by 29%. Then WMZ and WDZ are the relative proportions of these incidences. For example, at maternal age 20, WDZ is 60% and WMZ is 40%, whereas at age 40, WDZ is 84% and WMZ is 16%; in Afro-Caribbeans, the four proportions would be 70, 30, 89 and 11%.

The four maternal age-specific probabilities, $P_{x,DZ,1only}$, $P_{x,DZ,2only}$, $P_{x,DZ,both}$ and $P_{x,MZ}$, are expressed as odds (i.e. in the form P: 1-P) and multiplied by the appropriate likelihood ratios $LR_{1only}$, $LR_{2only}$ and $LR_{both}$. The result is re-expressed in percentage and the weighted average taken using $W_{DZ}$ and $W_{MZ}$. LRs express the relative probability of being affected compared to unaffected, for a given marker profile, hence the need to express prior probabilities as odds at that stage in the calculation. The probability that fetus 1 is affected is then, multiplying odds and probabilities as appropriate, $W_{DZ}(P_{x,DZ,1only}LR_{1only}+P_{x,DZ,both} LR_{both})+W_{MZ}P_{x,MZ} LR_{both}$, and the probability for fetus 2 is $W_{DZ} (P_{x,DZ,2only}LR_{2only}+P_{x,DZ,both} LR_{both})+W_{MZ}P_{x,MZ}LR_{both}$.

Figure 8:
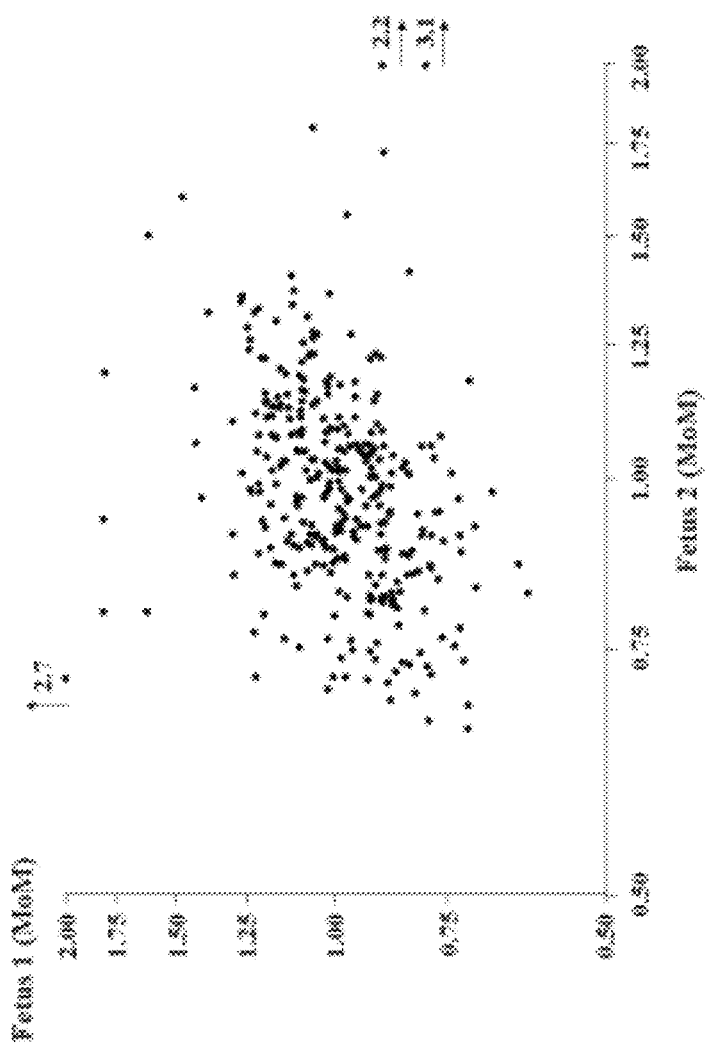
FIG. 8 is a graph showing paired nuchal translucency levels in 325 unaffected twin pregnancies, in accordance with certain examples.

FIG. 8 shows the individual pairs of NT MoM values for all 325 twins. The overall median was 0.99 MoM, the log 10 standard deviation was 0.072 and the correlation coefficient of log MoMs after excluding outliers was 0.43 (P<0.0001). According to operator, the correlation coefficient was 0.43 for 187 women scanned by one sonographer; 0.43, 62 by another sonographer; 0.58, 45 by a fetal medicine consultant and 0.14, 31 by another consultant. Analysis of variance yielded a correlation coefficient of 0.45 when stratified by operator and a covariance of 0.001811. There were 114 twins where the pregnancy followed IVF. The correlation coefficient was 0.52 compared with 0.38 in the remaining twins, not a statistically significant difference (P=0.44). Ultrasound information on chorionicity was available for 299 twins; the correlation coefficient was 0.43 for the 246 DC cases compared with 0.35 for the MC, also not statistically significant (P=0.76). The correlation coefficients in affected twin pregnancies are calculated by dividing the covariance in the unaffected pregnancies by the appropriate standard deviations. In those discordant for Down syndrome, it is 0.12 [0.001811/(0.21×0.070)], and in those which are concordant, it is 0.04 (0.001811/0.212).

Table 2 in FIG. 9 shows the fetus-specific risk in three examples where the NT is raised in one fetus but not in the other, or raised to a lesser extent. For each example, for the women aged 25 years, the NT scan was taken at 12 weeks but a range of possible ultrasound and clinical findings are considered. Before taking the scan, the maternal age-specific odds of Down syndrome are 1:1357 for fetus 1 alone, 1:1357 for fetus 2 alone, 1:273,618 for both fetuses in DZ and 1:1351 in MZ twins. To illustrate the method, consider Example 3 where the LRs are 12.40, 0.1210 and 1.322 for fetus 1 alone, fetus 2 alone and both fetuses, respectively. Therefore, after the scan, the four odds become 1:109, 1:11,215, 1:206,973 and 1:1022, or 0.9091, 0.0089, 0.0005 and 0.0978%, respectively. If this twin is DC and the fetuses are of the same gender, then as the age specific twinning incidence is 1.04%, the DZ and MZ weights are 73.88 and 26.12%. Hence, the probability of Down syndrome in fetus 1 is 73.88% of (0.9091+0.0005%) plus 26.12% of 0.0978%, which is 0.6976% or 1 in 140; for fetus 2, it is 73.88% of (0.0089+0.0005%) plus 26.12% of 0.0978%, which is 0.0325% or 1 in 3100. Table 2 demonstrates that there are very large differences in the risks obtained when the extent of correlation in NT between fetuses is taken into account and when the measurements are treated as independent. In some of these situations, it would have made a clinical difference and could have tipped the balance for the patient over whether to have invasive prenatal diagnosis. In practice, when there is ultrasound evidence of an MC pregnancy, some use the average of the two NT MoM values to calculate risk. However, in the three examples, this would not have yielded a correct risk: 1.7 and 1.5 MoM, 1 in 70; 1.7 and 1.0 MoM, 1 in 1100; 1.5 and 1.0 MoM, 1 in 2800. Some take the average of the two risks but this also yields inaccurate risks, even if the geometric mean is used: 1 in 70, 1 in 510 and 1 in 1700, respectively.

The above results are consistent with a correlation between the NT values in twin fetuses. As described above, a Down syndrome risk in a twin fetus can be calculated using its own NT and that of the co-twin. These risks can be substantially different from values obtained from the current method which incorrectly assumes that the two NTs are independent. In addition to the series from Denmark (Wøjdemann et al., 2006) where the correlation coefficient was 0.34, and our own where allowance was made for different operators and the correlation coefficient was 0.46, there is a small series where 29 paired NT and CRL values in unaffected MC twin pregnancies are tabulated (Casasbuenas et al., 2008). Using the normal median curve for Leeds (Logghe et al., 2003) to convert results into MoMs, the correlation coefficient of log MoM was 0.18.

Second-trimester severe twin-twin transfusion syndrome is not uncommon in MC twins and a large disparity in NT thickness between the fetuses is regarded as an early marker for the syndrome (Sebire et al., 1997). This could account for the mean disparity of 0.65 mm found in 105 MC twins compared with 0.49 mm in 176 DC twins (Cheng et al., 2010). However, this does not appear to be sufficient for the correlation coefficient to be lower in MC twins because the Danish series found the reverse (Wøjdemann et al., 2006). We have therefore used a single correlation coefficient for all types of unaffected twins.

There is little information on which to assess the correlation coefficient in affected twin pregnancies, whether discordant or concordant for Down syndrome. In the largest published study, in France, the NT and CRL values of 14 affected twins, all but one discordant, were tabulated (Garchet-Beaudron et al., 2008). Using the normal median curve for Leeds to convert results into MoMs, the correlation coefficient of log MoM in the discordant pairs was 0.89 (P<0.0001). Sixteen additional cases with NTs in twins discordant for Down syndrome are available from the literature—5 in MoMs (Spencer and Nicolaides, 2003; Gonć e et al., 2005) and 11 where NT and CRL pairs are given (Pandya et al., 1995; Sperling et al., 2007; Linskens et al., 2009)—and there was one screened at Leeds Screening Centre in the same period as the current series with NTs of 1.55 and 0.90 MoM. Combining the 14 French cases with these 17 cases using the latest Fetal Medicine Foundation curve (Wright et al., 2008) to convert the NT-CRL pairs into MoMs, the correlation coefficient of log MoM was 0.29 (P=0.13).

The French series is biased as a criterion for inclusion was that second-trimester maternal serum screening should be performed. Hence, cases with elevated NT would have tended to be excluded. Indeed, taking the largest MoM in each discordant pair to be from the affected fetus, the median value in the 15 affected fetuses was only 1.25 MoM and in the 13 unaffected fetuses was 1.03 MoM. Moreover, some of the correlations in the combined data of 31 cases would have been due to the inclusion of many sonographers, particularly as the French series was collected nationwide. In our method, we have assumed that the affected twins have the same covariance as the unaffected twins which yielded a correlation coefficient of 0.12 for discordant pairs which is consistent with the combined result taking into account these considerations.

There have been two reports in which the proportion of fetuses with NT thickness above the estimated CRL specific 95th centile was higher for twins than in singletons. In a study of 448 twins, the proportions were 7.3 and 5.4% (Sebire et al., 1996) and in a study of 100 twins, they were 9.0 and 4.2% (Monni et al., 2000). In a third study which included 174 twins, only 5.4% of fetuses had NT above the 95th centile, although the comparable proportion in singletons was not given (Maymon et al., 2001). A high proportion of large NTs in twins would suggest that either the average value of NT was higher than in singletons or there was a wider spread of values. However, in the Leeds Screening Centre series, neither the median (0.99 MoM) nor the log 10 standard deviation (0.072) is greater than for singletons. Hence, in our method, we have used the same median NT MoM and log standard deviations for affected and unaffected twin fetuses as for singletons.

There have been suggestions that the NT thickness is higher in MC twins than DC, possibly due to twin-twin transfusion (Sebire et al., 1996; Monni et al., 2000). However, others have found no significant differences according to the chorionicity in the screen-positive rate based on the NT (Maymon et al., 2001) or the median NT (Linskens et al., 2009). In a small series of 30 twins resulting from IVF or ICSI, the median NT was 10% lower than in 150 spontaneous twins, although not statistically significant (Orlandi et al., 2002). In another series, restricted to DC twins, the median NT was 1.02 in 54 resulting from assisted reproduction technologies and 1.07 in 38 spontaneous controls, again not statistically significant (Hui et al., 2006). There are no reliable data to directly estimate the age-specific probability of having twins concordant for Down syndrome and we have used an indirect approach. In a study from the National Down Syndrome Cytogenetic Register of England and Wales for the period 1989 to 1993, among 72 affected twins registered, 9 (12.5%) were concordant for Down syndrome, all of which had the same gender (Mutton et al., 1996). Using our approach at 32.7 years, the mean registered maternal age, the proportion expected to be concordant is 13.9% and of the same gender 13.8%. In another series of 27 affected twins with median age 35.5, 7 (25.9%) were concordant (Garchet-Beaudron et al., 2008) and using our approach the expected proportion was 12.7%.

We have assumed that the prior probability of an individual twin fetus having Down syndrome is the same as for a singleton. In a French nationwide study of Down syndrome screening in twins in 1998 to 2006, 34 of 22 080 fetuses were affected, an incidence of 1.5 per 1000 compared with 1.3 per 1000 in singletons (Garchet-Beaudron et al., 2008). Taking into account the maternal age difference—1 year older on average in the twins—and concordance in DZ twins, this is consistent with our assumption. Using national registration records in England and Wales in 1979 to 1985, 42 of 74 844 twin fetuses were found to have been registered as having Down syndrome (Doyle et al., 1990). After age standardization to a cohort of singleton births, the incidence was 0.50 per 1000 compared with 0.74 in the singletons. However, notification of congenital malformations is voluntary and there is considerable underreporting of Down syndrome. This is partly due to notification having to be made before 7 days of age, so under-ascertainment is likely to be greater for twins as a larger proportion will be stillborn. In a study of national registration records in Norway in 1967 to 1979, there were 13 affected twin fetuses out of 15 320, 0.85 per 1000 compared with 1.01 per 1000 in singletons (Windham and Bjerkedal, 1984). In Norway, registration is restricted to the time of birth allowing more chance of biased under-ascertainment. The only other large study of malformations in twins, in the United States, was based entirely on birth certificates, hence with substantial under-ascertainment of Down syndrome, and restricted to live births (Hey and Wehrung, 1970). In twins following SET, we have assumed that all are MZ. In one study of SET where zygocity is explicitly stated, the only twin is reported as MZ (Gerris et al., 1999); however, in another study, there were three twins of which one was reported as DZ and a fourth which spontaneously reduced to a singleton was also reported as DZ (Sundstrom and Saldeen, 2009). The most likely explanation is that these two cases were in fact DC as the authors do not discuss this unexpected finding or state how they established zygocity. If two of five were truly DZ, then applying the same logic as we used for MET, in DC twins of the same gender following IVF with SET, the weights would be taken to be WDZ 46% and WMZ 54%.

In spontaneous twins, we have used information on maternal age-specific incidence of twinning in 1960, prior to the widespread use of assisted reproduction technologies, to estimate WDZ and WMZ. Similarly, data from 1980 were used to estimate these weights in women of Afro-Caribbean origin. There is also evidence that the prevalence of twinning is higher in first-degree relatives of twins (Bortolus et al., 1999). This factor was not used in the method but it could readily be included. Fetal gender can be determined by ultrasound at the time of the NT scan. However, if this information is not available, different WDZ and WMZ values are needed. In DC twins where IVF was carried out with MET, the values are 99.6 and 0.4%. For spontaneous pregnancies, the formulae in Table 1 are modified by deleting the 0.51 factor.

As more data become available, our method for calculating Down syndrome risk from NT in twins can be improved. For example, more directly observed values will establish more accurate estimates of the correlation coefficient in twins discordant and concordant for Down syndrome. Meanwhile, the parameters in this article are reliable enough for our method to immediately replace the current clinical practice which incorrectly assumes that the NT measurements in the two fetuses are independent.

Certain references are referred to herein. The complete citation for these references is provided below for convenience:

Bortolus R, Parazzini F, Chatenoud L, Benzi G, Bianchi M M, Marini A. 1999. The epidemiology of multiple births. Hum Reprod Update 5(2): 179-187.

Bulmer, M G. The biology of twinning in man. Clarendon Press, Oxford: 1970.

Casasbuenas A, Wong A E, Sepulveda W. 2008. Nuchal translucency thickness in monochorionic multiple pregnancies: value in predicting pregnancy outcome. J Ultrasound Med 27(3): 363-369.

Cheng P J, Huang S Y, Shaw S W, Hsiao C H, Kao C C, Chueh H Y, Hsieh T T. 2010. Difference in nuchal translucency between monozygotic and dizygotic spontaneously conceived twins. Prenat Diagn. 30(3): 247-250.

Cuckle H, Benn P. 2010. Multianalyte maternal serum screening for chromosomal defects. In Genetic Disorders and the Fetus: Diagnosis, Prevention and Treatment (6th edn), Milunsky A, Milunsky J M (eds). Johns Hopkins University Press: Baltimore; 771-818.

Cuckle H S, Wald N J, Thompson S G. Estimating a woman's risk of having a pregnancy associated with Down's syndrome using her age and serum alpha-fetoprotein level. Br J Obstet Gynaecol 1987; 94,387-402.

Doyle P E, Beral V, Botting B, Wale C J. Congenital malformations in twins in England and Wales. J Epid Comm Health 1990; 45:43-48.

Elwood J M. Maternal and environmental factors affecting twin births in Canadian cities. Br J Obstet Gynaecol. 1978; 85(5):351-8.

Garchet-Beaudron A, Dreux S, Leporrier N, Oury J F, Muller F; ABA Study Group; Clinical Study Group. Second-trimester Down syndrome maternal serum marker screening: a prospective study of 11 040 twin pregnancies. Prenat Diagn. 2008; 28(12):1105-9.

General Register Office. The Registrar General's Statistical Review of England and Wales for the year 1960. Part 2: Tables, Population. Pp. xi+180. London: Her Majesty's Stationery Office, 1962.

Gerris J, De Neubourg D, Mangelschots K, Van Royen E, Van de Meerssche M, Valkenburg M. Prevention of twin pregnancy after in-vitro fertilization or intracytoplasmic sperm injection based on strict embryo criteria: a prospective randomized clinical trial. Hum Reprod. 1999; 14(10):2581-7.

Goncé A, Borrell A, Fortuny A, et al. First-trimester screening for trisomy 21 in twin pregnancy, does the addition of biochemistry make an improvement? Prenat Diagn 2005; 25:1156-1161.

Hey S, Wehrung D A. Congenital malformations in twins. Am J Hum Genet 1970; 22:662-678.

Hui P W, Tang M H, Ng E H, Yeung W S, Ho P C. Nuchal translucency in dichorionic twins conceived after assisted reproduction. Prenat Diagn 2006; 26(6):510-513.

Linskens I H, Spreeuwenberg M D, Blankenstein M A, van Vugt J M. Early first-trimester free beta-hCG and PAPP-A serum distributions in monochorionic and dichorionic twins. Prenat Diagn. 2009; 29(1):74-8.

Logghe H, Cuckle H, Sehmi I 2003. Centre-specific ultrasound nuchal translucency medians needed for Down's syndrome screening. Prenat Diagn 23: 389-392.

Loos R, Derom K, Vlietinck R, Derom R. 1998. East Flanders Prospective Twin Survey (Belgium): a population-based register. Twin Res 1: 167-175.

Machin G, Bamforth F, Innes M, McNichol K. Some perinatal characteristics of monozygotic twins who are dichorionic. Am J Med Genet 1995; 55(1):71-6.

Maymon R, Jauniaux E, Holmes A, Weiner Y M, Dreazen E, Herman A. Nuchal translucency measurement and pregnancy outcome after assisted conception versus spontaneously conceived twins. Hum Reprod 2001; 16(9):1999-2004.

Meyers C, Adam R, Dungan J, Prenger V. Aneuploidy in twin gestations, when is maternal age advanced? Obstet Gynecol 1997; 89:248-251.

Monni G, Zoppi M A, Ibba R M, Putzolu M, Floris M. Nuchal translucency in multiple pregnancies. Croat Med J. 2000; 41(3):266-9.

Mutton D, Alberman E, Hook E B. Cytogenetic and epidemiological findings in Down syndrome, England and Wales 1989 to 1993. National Down Syndrome Cytogenetic Register and the Association of Clinical Cytogeneticists. J Med Genet 1996; 33(5): 387-394.

National Center for Health Statistics. Vital and Health Statistics. Health and demographic characteristics of twin births: United States 1988. Hyattsville, Md., DHHS Publication Bo. (PHS) 92-1928: 1992.

Orlandi F, Rossi C, Allegra A, Krantz D, Hallahan T, Orlandi E, Macri J. First trimester screening with free beta-hCG, PAPP-A and nuchal translucency in pregnancies conceived with assisted reproduction. Prenat Diagn. 2002; 22(8):718-21.

Pandya P P, Hilbert F, Snijders R J M, Nicolaides K H. Nuchal translucency thickness and crown-rump length in twin pregnancies with chromosomally abnormal fetuses. J Utrasound Med 1995; 14: 565-568.

Russell R B, Petrini J R, Damus K, Mattison D R, Schwarz R H. 2003. The changing epidemiology of multiple births in the United States. Obstet Gynecol 101(1): 129-135.

Sebire N J, Snijders R J M, Hughes K, Sepulveda W, Nicolaides K H. Screening for trisomy 21 in twin pregnancies by maternal age and fetal nuchal translucency thickness at 10-14 weeks of gestation. Br J Obstet Gynaecol 1996; 103: 999-1003.

Sebire N J, D'Ercole C, Hughes K, Carvalho M, Nicolaides K H. Increased nuchal translucency thickness at 10-14 weeks of gestation as a predictor of severe twin-to-twin transfusion syndrome. Ultrasound Obstet Gynecol. 1997; 10(2): 86-9.

Spencer K, Nicolaides K H. Screening for trisomy 21 in twins using first trimester ultrasound and maternal serum biochemistry in a one-stop clinic: a review of three years experience. Br J Obstet Gynaecol. 2003; 110(3):276-80.

Spencer K, Bindra R, Nix A B, Heath V, Nicolaides K H. Delta-NT or NT MoM, which is the most appropriate method for calculating accurate patient-specific risks for trisomy 21 in the first trimester? Ultrasound Obstet Gynecol 2003; 22:142-148.

Sperling L, Kiil C, Larsen L U, et al. 2007. Detection of chromosomal abnormalities, congenital abnormalities and transfusion syndrome in twins. Ultrasound Obstet Gynecol 29(5): 517-526.

Stenhouse E, Hardwick C, Maharaj S, Webb J, Kelly T, Mackenzie F M. Chorionicity determination in twin pregnancies, how accurate are we? Ultrasound Obstet Gynecol 2002; 19(4):350-352.

Sundström P, Saldeen P. Cumulative delivery rate in an in vitro fertilization program with a single embryo transfer policy. Acta Obstet Gynecol Scand. 2009; 88(6):700-6.

Vitthala S, Gelbaya T A, Brison D R, Fitzgerald C T, Nardo L G. The risk of monozygotic twins after assisted reproductive technology: a systematic review and meta-analysis. Hum Reprod Update. 2009; 15(1):45-55.

Windham G C, Bjerkedal T. Malformations in twins and their siblings, Norway, 1967-79. Acta Genet Med Gemellol (Roma) 1984; 33(1):87-95.

Wøjdemann K R, Larsen S O, Shalmi A C, Sundberg K, Tabor A, Christiansen M. 2006. Nuchal translucency measurements are highly correlated in both mono- and dichorionic twin pairs. Prenat Diagn 26(3): 218-220.

Wright D, Kagan K O, Molina F S, Gazzoni A, Nicolaides K H. A mixture model of nuchal translucency thickness in screening for chromosomal defects. Ultrasound Obstet Gynecol. 2008; 31 (4):376-383.

Wright V, Schieve L A, Vahratian A, Reynolds M A. 2004. Monozygotic twinning associated with day 5 embryo transfer in pregnancies conceived after IVF. Hum Reprod 19(8): 1831-1836.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A ultrasound system comprising:
an ultrasound transducer; and
a processor electrically coupled to the ultrasound transducer and configured to determine nuchal translucency values for each of a first fetus of twin fetuses and a second fetus of twin fetuses and provide a risk of a chromosomal abnormality in each of the first fetus and the second fetus of twin fetuses by determining a first, second and third determined likelihood ratio using the nuchal translucency values and using a between-fetus nuchal translucency correlation, in which the processor is configured to determine the first likelihood ratio based on the first fetus including the chromosomal abnormality and a second fetus being normal, is configured to determine the second likelihood ratio based on the first fetus being normal and the second fetus including the chromosomal abnormality and is configured to determine the third likelihood ratio based on the first fetus including the chromosomal abnormality and the second fetus including the chromosomal abnormality.

2. The ultrasound system of claim 1, further comprising a memory unit electrically coupled to the processor and configured to receive the nuchal translucency values, the processor configured to apply a bivariate Gaussian distribution on the nuchal translucency values received by the memory unit to determine the first, second and third likelihood ratios.

3. The ultrasound system of claim 2, in which the processor is configured to apply independently selectable weighting factors to the nuchal translucency values received by the memory unit to determine the first, second and third likelihood ratios.

4. The ultrasound system of claim 3, in which the system comprises a graphical user interface configured to permit selection of the independently selectable weighting factors.

5. The ultrasound system of claim 1, further comprising a display screen configured to display signals from the ultrasound transducer.

6. The ultrasound system of claim 5, in which the signals are displayed as a two-dimensional image.

7. The ultrasound system of claim 6, in which pixel positions of the display screen are used to determine the nuchal translucency values.

8. The ultrasound system of claim 7, in which the determined nuchal translucency values are determined automatically by marking pixel positions on the two-dimensional image.

9. The ultrasound system of claim 7, in which the risk of a chromosomal abnormality in each of a first fetus and a second fetus of twin fetuses is determined automatically by marking pixel positions on the two-dimensional image.

10. The system of claim 1 in which the processor is configured to determine each of the likelihood ratios using the equation $$LR = \left[\frac{s_{u1}s_{u2}\sqrt{(1-r_u^2)}}{s_{a1}s_{a2}\sqrt{(1-r_a^2)}}\right] \times \exp\left[\frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)}\right]$$

where s is the standard deviation, r is the correlation coefficient, z is [(log$_{10}$MoM−mean)/s], u represents unaffected, a represents affected and 1 and 2 represent the first fetus and the second fetus, respectively.

11. The system of claim 1, in which each of the likelihood ratios is calculated using the mother's age, mother's race, chorionicity and whether assisted reproduction treatments were obtained.

12. A method of assessing a risk of a chromosomal abnormality in twin fetuses using nuchal translucency measurements from a first fetus and a second fetus of the twin fetuses, the method comprising:

using a processor to perform the steps of
determining a first likelihood ratio from nuchal translucency measurements of the first fetus and the second fetus based on the first fetus including the chromosomal abnormality and the second fetus being normal, wherein the first likelihood ratio is determined using a between-fetus nuchal translucency correlation of the nuchal translucency measurements used to determine the first likelihood ratio;
determining a second likelihood ratio from the nuchal translucency measurements of the first fetus and the second fetus based on the first fetus being normal and the second fetus including the chromosomal abnormality, wherein the second likelihood ratio is determined using a between-fetus nuchal translucency correlation of the nuchal translucency measurements used to determine the second likelihood ratio;
determining a third likelihood ratio from the nuchal translucency measurement of the first fetus and the second fetus based on the first fetus including the chromosomal abnormality and the second fetus including the chromosomal abnormality, wherein the third likelihood ratio is determined using a between-fetus nuchal translucency correlation of the nuchal translucency measurements used to determine the third likelihood ratio; and
determining the risk of the chromosomal abnormality in each of the first fetus and the second fetus using the first, second and third determined likelihood ratios.

13. The method of claim 12, in which the first, second and third likelihood ratios are determined from nuchal translucency ultrasound measurements of the first fetus and the second fetus and by using a bivariate log Gaussian distribution.

14. The method of claim 12, in which the first, second and third likelihood ratios are determined from nuchal translucency magnetic resonance imaging measurements of the first fetus and the second fetus.

15. The method of claim 12, in which each of the first, second and third likelihood ratios are individually weighted to determine the risk of the chromosomal abnormality.

16. The method of claim 15, in which weighting factors based on at least one of maternal age, use of assisted reproductive technologies, ethnicity, history, chorionicity, and fetus gender are used to weight the likelihood ratios.

17. The method of claim 12, further comprising performing at least one blood test to determine a risk of the chromosomal abnormality and comparing the risk determined from the blood test with the risk determined using the first, second and third determined likelihood ratios.

18. The method of claim 12, further comprising performing amniocentesis to determine a risk of the chromosomal abnormality and comparing the risk determined from the amniocentesis with the risk determined using the first, second and third determined likelihood ratios.

19. The method of claim 12, further comprising performing chorionic villi sampling to determine a risk of the chromosomal abnormality and comparing the risk determined from the blood test with the risk determined using the first, second and third determined likelihood ratios.

20. The method of claim 12, further comprising comparing the determined risk with a risk determined using logistic regression.

21. The method of claim 12, in which each the likelihood ratio is determined using the equation $$LR = \left| \frac{s_{u1}s_{u2}\sqrt{(1-r_u^2)}}{s_{a1}s_{a2}\sqrt{(1-r_a^2)}} \right| \times \exp\left[ \frac{(z_{u1}^2 + z_{u2}^2 - 2r_u z_{u1} z_{u2})}{2(1-r_u^2)} - \frac{(z_{a1}^2 + z_{a2}^2 - 2r_a z_{a1} z_{a2})}{2(1-r_a^2)} \right]$$

where s is the standard deviation, r is the correlation coefficient, z is [($\log_{10}$MoM−mean)/s], u represents unaffected, a represents affected and 1 and 2 represent the first fetus and the second fetus, respectively.

22. The method of claim 12, in which each of the likelihood ratios is calculated using the mother's age, mother's race, chorionicity and whether assisted reproduction treatments were obtained.

* * * * *